United States Patent [19]

Ramsey, III et al.

[11] Patent Number: 4,638,810

[45] Date of Patent: Jan. 27, 1987

[54] AUTOMATED DIASTOLIC BLOOD PRESSURE MONITOR WITH DATA ENHANCEMENT

[75] Inventors: Maynard Ramsey, III, Tampa; Richard Medero, Lutz; Rush W. Hood, Jr., Tampa, all of Fla.

[73] Assignee: Critikon, Inc., Tampa, Fla.

[21] Appl. No.: 751,825

[22] Filed: Jul. 5, 1985

[51] Int. Cl.[4] .................................................. A61B 5/02
[52] U.S. Cl. ........................................ 128/681; 128/682
[58] Field of Search .................................. 128/680–683

[56] References Cited

U.S. PATENT DOCUMENTS 4,407,297 10/1983 Croslin .................................... 128/681
4,592,365 6/1986 Georgi .................................... 128/680

OTHER PUBLICATIONS

Link, W. T., "Norse Systems BP Monitor", Company Memorandum, received 11/1974.

Primary Examiner—Kyle L. Howell
Assistant Examiner—Francis J. Jaworski
Attorney, Agent, or Firm—Audley A. Ciamporcero, Jr.

[57] ABSTRACT

A blood pressure cuff is applied about a subject's artery, and inflated above the systolic level thus fully occluding the artery for a full heart cycle. The cuff pressure is thereafter reduced to permit an increasing flow through the progressively less occluded artery, and a measure of the peak amplitudes of the successively encountered blood flow (oscillatory complex) pulses stored in memory. Also retained is the cuff pressure obtaining for each stored complex peak. In accordance with varying aspects of the present invention, the stored complex peak-representing data ensemble is corrected for aberrations; and improved data processing operates on the stored (and advantageously corrected) pulse peak data and the corresponding cuff pressure information to determine the subject's diastolic arterial blood pressure.

9 Claims, 9 Drawing Figures

FIG-4  SYSTOLIC DETERMINATION

FIG-7 DIASTOLIC DETERMINATION

FIG-9

AUTOMATED DIASTOLIC BLOOD PRESSURE MONITOR WITH DATA ENHANCEMENT

FIELD OF THE INVENTION

This invention relates to automated blood pressure measuring apparatus and, more particularly, to stored program controlled monitors employing the oscillometric method of detection characterized by data purification and enhanced systolic, diastolic and mean blood pressure determination.

CROSS REFERENCE TO RELATED APPLICATIONS

Reference is hereby made to the following concurrently filed co-pending commonly assigned patent applications: IMPROVED SPHYGMOMANOMETRIC CUFF PRESSURIZING SYSTEM, Ramsey et al., Ser. No. 751,835; OSCILLOMETRIC BLOOD PRESSURE MONITOR EMPLOYING NON-UNIFORM PRESSURE DECREMENTING STEPS, Ramsey et al. Ser. No. 751,840; IMPROVED AUTOMATED MEAN ARTERIAL BLOOD PRESSURE MONITOR WITH DATA ENHANCEMENT, Ramsey et al., Ser. No. 751,826; IMPROVED AUTOMATED SYSTOLIC BLOOD PRESSURE MONITOR WITH DATA ENHANCEMENT, Ramsey et al., Ser. No. 751,827.

BACKGROUND OF THE INVENTION

Automated blood pressure monitoring has rapidly become an accepted and, in many cases, essential aspect of human and veterinary treatment. Such monitors are now a conventional part of the patient environment in emergency rooms, intensive and critical care units, and in the operating theatre.

The so-called oscillometric method of measuring blood pressure is one of the most popular methods in commercially available systems. This method relies on measuring changes in arterial counterpressure, such as imposed by an inflatable cuff, which is controllably relaxed or inflated. In some cases the cuff pressure change is continuous, and in others it is incremental. In substantially all, a transducer monitors arterial counterpressure oscillations, and processing apparatus converts select parameters of these oscillations into blood pressure data.

Of particular interest with respect to the principles of the present invention are the concepts set forth in U.S. Pat. Nos. 4,360,029 and 4,394,034 to M. Ramsey, III, which are commonly assigned with the instant invention. The Ramsey patents derive from common parentage, the former including apparatus claims and the latter including method claims, their division having been made in response to a restriction requirement during the prosecution. Both patents, however, carry common disclosures of apparatus and methods for artifact rejection in oscillometric systems, which have been in practice in the commercially successful DINAMAP brand monitors, which are manufactured and marketed by Critikon, Inc., of Tampa, Fla., the assignee hereof. In accordance with the Ramsey patents, an inflatable cuff is suitably located on the limb of a patient, and is pumped up to a predetermined pressure. Thereupon, the cuff pressure is reduced in predetermined fixed decrements, at each level of which pressure fluctuations are monitored. These typically consist of a DC voltage with a small superimposed variational component caused by arterial blood pressure pulsations (referred to herein as "oscillatory complexes"). Therefore, after suitable filtering to reject the DC component and to provide amplification, pulse peak amplitudes above a given threshold are measured and stored. As the decrementing continues, the peak amplitudes will normally increase from a lower amount to a relative maximum, and thereafter will decrease. The lowest cuff pressure at which the oscillations have a maximum peak value is representative of mean arterial pressure. The cuff pressures obtaining when stored oscillatory complex pulse peak amplitudes bear predetermined fractional relationships with the largest stored peak corresponding to the subject's systolic and diastolic pressures.

The Ramsey patents devote considerable effort and disclosure to the rejection of artifact data to derive accurate blood pressure data. Indeed, as is apparent from FIG. 2 of the Ramsey patents, the most substantial portion of the measurement cycle (denominated "T3") is devoted to the execution of complex detection at the various pressure levels, measurement of signal peaks of true complexes, and processing those peaks in accordance with artifact rejection algorithms. Notwithstanding such efforts, the signal peak data collected sometimes incorporates data errors, i.e., a data pattern inconsistent with the above described typical physiological response pattern of a subject as the artery occluding cuff pressure monotonically decreases.

Further, in a contemporaneous invention (see M. Ramsey III, et al patent application Ser. No. 751,840 for "OSCILLOMETRIC BLOOD PRESSURE MONITOR EMPLOYING NON-UNIFORM PRESSURE DECREMENTING STEPS" filed on even date herewith, the disclosure of which is incorporated herein by reference) oscillometric blood pressure measurements are effected with non-uniform, cuff pressure-dependent pressure decrements between successive oscillatory complex peak measuring intervals. Such a method of effecting oscillometric blood pressure measurements is facilitated by systolic, diastolic and mean blood pressure determining algorithms not heretofore employed.

It is an object of the present invention to provide improved oscillometric blood pressure determining apparatus and methodology.

More specifically, it is an object of the present invention to purify the oscillatory complex peak amplitude data ensemble employed for blood pressure determination.

Yet another object of the present invention is the provision of improved algorithms, methodology and apparatus for determining diastolic blood pressure.

SUMMARY OF THE INVENTION

A blood pressure cuff is applied about a subject's artery, and inflated above the systolic level thus fully occluding the artery for a full heart cycle. The cuff pressure is thereafter reduced to permit an increasing flow through the progressively less occluded artery, and a measure of the peak amplitudes of the successively encountered oscillatory complexes stored in memory. Also retained is the cuff pressure obtaining for each stored complex peak.

In accordance with varying aspects of the present invention, the stored complex peak-representing data set is corrected for aberrations; and improved data processing operates on the stored (and advantageously corrected) pulse peak data and the corresponding cuff pressure information to determine the subject's, diastolic pressure.

DESCRIPTION OF THE DRAWINGS

The above and other objects and features of the present invention will be realized from the following detailed discussion of a specific, illustrative embodiment thereof, presented hereinbelow in conjunction with the accompanying drawing, in which.

BEST MODE FOR CARRYING OUT THE INVENTION

U.S. Pat. Nos. 4,360,029 and 4,349,034, each to Maynard Ramsey, III, and pending Maynard Ramsey, III et al application U.S. Pat. No. 4,543,962 for "IMPROVED METHOD OF AUTOMATED BLOOD PRESSURE DETECTION" issued Oct. 1, 1985 are incorporated herein by reference, as is the aforementioned co-filed Ramsey III et al application. These patents and patent applications describe in detail the basic oscillometric method of measuring blood pressure forming a background and a starting point for the instant invention.

To review only briefly, an artery-occluding cuff is disposed on the subject, e.g., about a subject's upper arm over the brachial artery. At the inception of a measuring cycle, the cuff is inflated to a pressure which fully occludes the brachial artery, i.e., prevents blood from flowing therethrough at any point in the heart cycle. The cuff is then progressively deflated, as in discrete steps. A pressure transducer is coupled to the internal cuff pressure and provides an analog signal characterizing the blood pressure oscillatory complexes when they begin to occur (i.e., when the maximum heart pressure corresponding to contraction of the heart's left ventricle exceeds the instantaneously obtaining artery-occluding cuff pressure). The peak values of the complex signals are determined in hardware or software.

As the measurement cycle progresses, the peak amplitude of the blood pressure complexes generally become monotonically larger to a maximum and then become monotonically smaller as the cuff pressure continues toward deflation. The peak amplitude of the cuff pressure oscillation complexes, and the corresponding occluding-cuff pressure values are retained in computer memory. The aforementioned Ramsey patents and patent applications illustrate previously employed algorithms for processing the stored blood pressure complex peak values and concomitant pressure values to yield the subject's mean arterial pressure. These patents and applications also furnish detailed procedures for measuring oscillatory complex peaks; procedures for testing complexes and rejecting bad data associated with measurement-impeding artifacts (such as motion) during a measuring cycle, and the like.

The oscillometric blood pressure measurements as typified by the aforementioned Ramsey disclosures are effected under stored program control, as via a microprocessor operative in conjunction with a program containing read only memory (ROM or PROM), and a variable content random access memory (RAM) which stores the cuff pressures, oscillatory complex peak amplitudes, and other processing operand variables. The microprocessor receives the cuff pressure readings generated by the pressure transducer, for example as processed by a peak detector, amplifier and analog-to-digital converter, and supplies all output control signals required, e.g., to open and close one or more cuff deflating valves.

The oscillometric method above described and more fully discussed in the aforementioned Ramsey patents and applications may be conducted with several variations. Thus, for example, the cuff may be inflated directly by an air pump; and deflated in fixed, discrete steps under microprocessor control. Alternatively, the cuff may be principally or entirely inflated by the presurized contents of an air reservoir; and/or deflation may proceed in variable, cuff pressure-dependent steps via selected one or ones of plural deflating valves. These latter alternatives achieve the desideratum of condensing the time required for a composite measurement cycle of operation.

Also, there are alternative procedures for measuring the oscillatory complex peak amplitude at any prevailing cuff pressure. In one mode heretofore employed, plural (e.g., two) complex peaks are measured at each cuff pressure step during cuff deflation, and their average used as the peak value. Since the peaks should be approximately equal, any marked disparity (e.g., >20%) signals that some artifact error occurred and the data is rejected. In a fast ("stat") mode, after several intervals of qualifying (close or equal peak values) companion complexes are detected to develop measurement confidence, only one pulse is required during succeeding cuff deflation intervals thus speeding the composite measurement period. Please see in this later regard the aforementioned application filed July 9, 1984.

As alluded to above, it is sometimes the case when blood pressure complexes are being examined for peak amplitude at any occluding pressure level that improper data is developed. There are varying causes for such aberrations. Perhaps the most common is spurious motion by the subject which generates an inadvertent pressure impulse in the cuff which is sensed by the pressure transducer which may be then incorrectly reflected in the blood pressure measurement. Other causes include varying sources of interfering electrical noise or internal cardiac or respiratory changes in the subject. When a false complex peak amplitude value is generated, it is discarded by the composite measuring apparatus and a discard-signalling value (e.g., +1) retained in its place in memory.

A second form of spurious data occurs when the pattern of stored pulse peak values departs from the physiologically mandated sequence of values which progressively increase to a peak and then progressively decrease.

Attention will now be directed to data processing under stored program control for purifying the data collected by the above-described blood pressure measuring apparatus. Further, specific illustrative efficient algorithms are discussed for in fact determining the subject's systolic, diastolic and mean arterial blood pressures. Such data processing may be effected on any computing equipment, preferably digital microprocessors such as commercially available from a number of vendors. The program instructions and sequences presented below are for illustrative purposes only. Such instructions may in fact be implemented in any of diverse program languages and sequences readily apparent to those skilled in the art. In the signal processing below discussed, processing variables have the following significance:

| Variable | Functional Quantity Represented |
|---|---|
| I. Variables Employed For All Data Processing Below Discussed | |
| CP(I) | The cuff pressure, measured by the transducer pneumatically coupled to the artery occluding cuff, obtaining during the i-th deflation step. CP(I) is an indexed array, i.e., there exists a plurality of values for CP(I) characterizing each of the i deflation steps. |
| φA(I) | The peak amplitude of the oscillometric oscillation (i.e., the complex peak amplitude) occurring at the i-th step. Where multiple complexes are measured during each prevailing deflation pressure, φA(I) is the average of two (or more) peak amplitudes during the i-th step. φA(I) is an indexed array. |
| φA(MAX) | The peak value of the array of averaged oscillatory blood pressure complex amplitudes. |
| MAX | The time interval when the peak complex φA(MAX) occurred. |
| II. Variables Specific To Systolic Pressure Measurement | |
| LVL | An intermediate processing variable representing a predetermined fraction of φA(MAX). |
| SYS | The subject's measured systolic pressure. |
| III. Diastolic Pressure Variables | |
| UDLVL and LDLVL | Intermediate processing variables each representing a different fraction of φA(MAX). |
| DIAU, DIAL | Intermediate processing variables representing upper and lower interpolated diastolic pressure computational variables. |
| DIA | The subject's measured diastolic pressure. |
| IV. Mean Arterial Pressure Processing Variables | |
| AMP | The complex pulse peak for the deflation interval following that for which the pressure oscillation amplitude was the maximum. |
| MAPL | An intermediate processing variable employed in the final mean arterial pressure computation. |
| MAP | The subject's mean arterial blood |

| Variable | Functional Quantity Represented |
|---|---|
| | pressure. |

Figure 1:
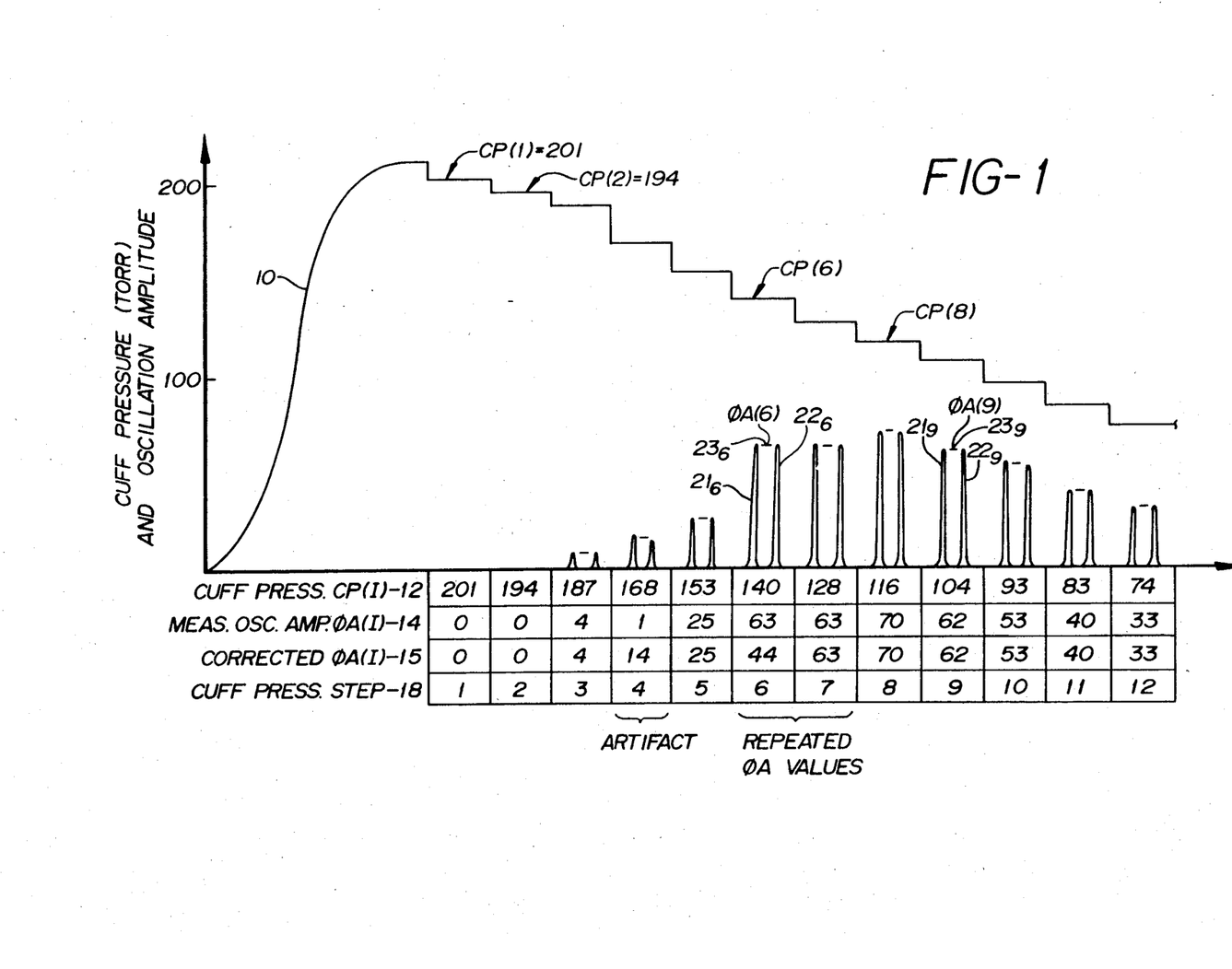
FIG. 1 is a timing diagram illustrating data generation and correction during an illustrative measurement cycle for oscillometric blood pressure determination in accordance with the principles of the present invention.

Turning now to FIG. 1, there is depicted wave forms with associated data characterizing the generation of data for an oscillatory blood pressure measurement—and purging (overcoming) bad data constituents. In accordance with the above discussion, the cuff artery occluding pressure for a measurement cycle, as measured by the cuff-associated transducer, is characterized by a wave form 10. The cuff pressure rapidly increases to a maximum above the subject's systolic pressure, and is then deflated in a sequence of steps to a point below the diastolic pressure. The sequence of cuff deflation steps is indicated by the time interval signalling digits 1, 2, ..., (lowest row 18 in the data table portion of FIG. 1). The internal pressure characterizing the cuff pressure at each step i is given by the data array CP(1), CP(2), ... (upper data table row 12).

Each step (time interval) is made sufficiently long to include at least two heart beats. Accordingly, at least two cuff pressure complex pulses $21_i$ and $22_i$ are measured during each interval after such pulses begin. Legends have been applied to pulses occurring during deflation steps 6 and 9 to avoid clutter and loss of clarity in FIG. 1. No pulses are measured during the first and second pressure steps (time intervals), it being assumed that the cuff pressure [CP(1)=201 Torr., and CP(2)=194 Torr.] are sufficient during these periods to obviate blood flow through the subject's artery for the full heart cycle. During the following intervals 3, 4 ..., two oscillometric complex pulses $21_i$ and $22_i$ are generated and measured, the two pulses having an average peak amplitude $23_i$ (the processor variable array value initially stored in ΦA(I)). The *measured* oscillation amplitude array (ΦA(I)) is shown in the second row 14 of the FIG. 1 data table for each time interval.

As above noted, assuming a perfect measurement, the oscillation pressure amplitude ΦA(I) data row would not contain any +1 values which signify an impeded measurement. Further, the data pattern in the second row of the data table for the oscillation amplitudes would exhibit a pattern of successively increasing numbers to a peak value, followed by progressively decreasing values—all without adjacent equal ΦA(I) values. To the extent that any ΦA(I)=1 values are stored, or to the extent that the progressively increasing/decreasing pattern does not obtain, the data processing in accordance with the instant invention functions to compute appropriate corrected ΦA(I) values (the third data table row 15 in FIG. 1) for the oscillation amplitude entries requiring correction.

In overview, where any ΦA(I)=1 values exist, they are replaced by the average value of the oscillation amplitude in the two contiguous storage cells, i.e., $$\Phi A(I) = (\Phi A(I-1) + \Phi A(I+1))/2. \qquad \text{Eq. 1.}$$

Correspondingly, where two contiguous oscillation amplitudes have the proscribed equal values, the first of the contiguous equal pair is replaced by the average of the amplitudes of the complex peaks measured at the next lower and next higher occluding cuff pressures. See, for example, Eq. 1 and, more particularly, the comparable relationship in functional block 30 of FIG. 2.

Figure 2:
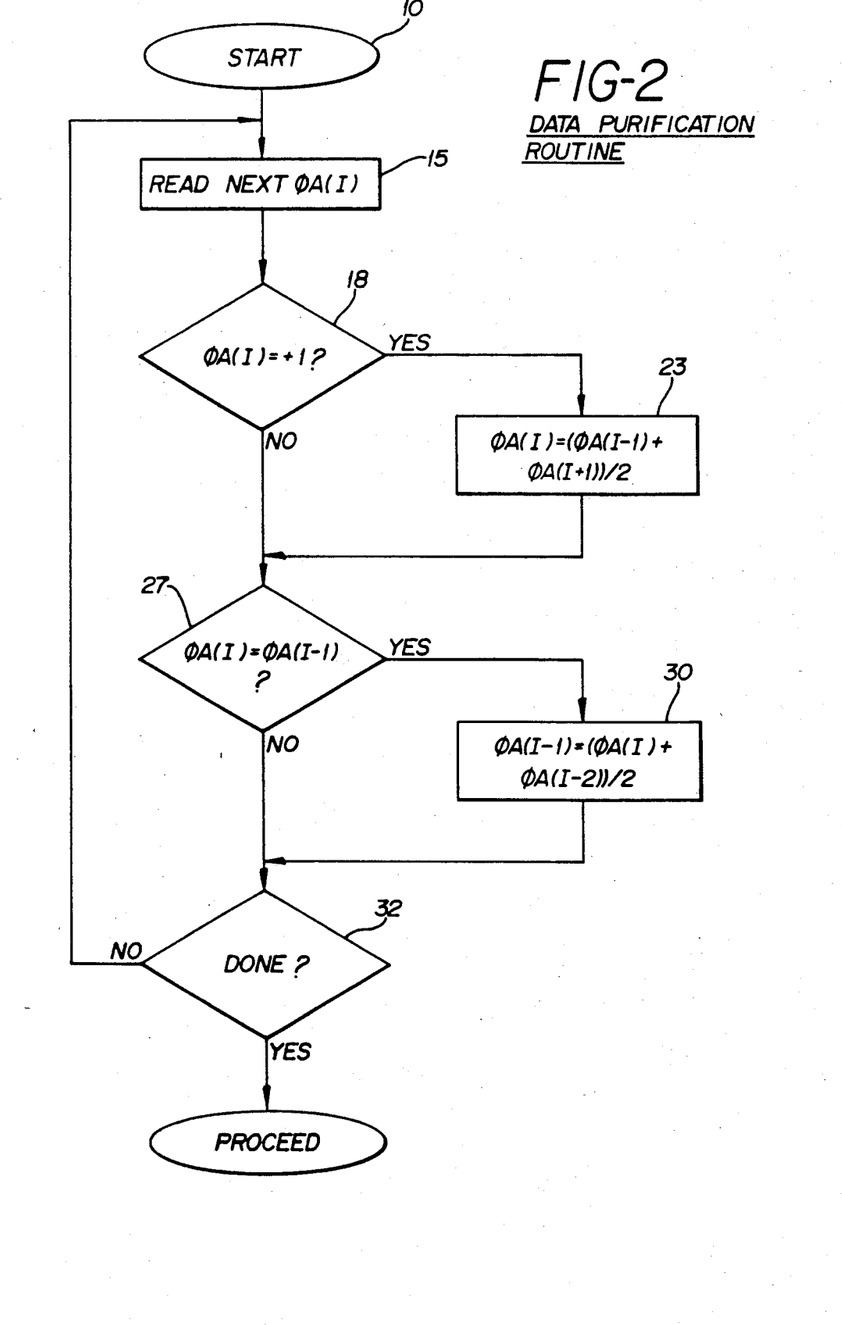
FIG. 2 is a flow chart illustrating data purification for improved oscillometric blood pressure determination.

Data flow effecting the data purification algorithm above-discussed is set forth in the program flow chart of FIG. 2. FIG. 2 operates on the measured average oscillation amplitudes (the second data table row 14 in FIG. 1) and generates the corrected ΦA(I) values shown in the third row 15 of FIG. 1. To this end, proceeding from a start block 10 (FIG. 2), step 15 reads the next value ΦA(I) (proceeding toward the right along the FIG. 1 data table row 14) and test 18 determines whether the value stored in ΦA(I) equals the error-signalling value +1. If as is the usual case it does not (indicating that the value measured was presumptively free of artifacts and the like), control passes to equality test 27. However, if the contents of ΦA(I) did equal +1 ("YES" branch of test 18), functional block 23 implements Eq. 1, i.e., replaces the +1 former contents of memory cell ΦA(I) corresponding to cuff pressure CP(I) with the average value of the oscillation amplitude measured at the next lower (ΦA(I−1)) and next higher non-plus one (ΦA(I+1)) deflation steps. The processing steps 18 and 23 thus purge the measured pressure peak amplitude storage contents (the second row of the FIG. 1 data table) of all +1 values, replacing these by the average value of the measurements made during immediately adjacent deflation steps (corrected ΦA(I) contents being illustrated in row Test 27 next examines the current operand ΦA(I) for the proscribed equality with the previous value ΦA(I−1). If, as is normally the case, the contents of ΦA(I) and ΦA(I−1) differ ("NO" branch from test 27), processing flows to test 32 to determine whether each of the N elements of ΦA(I) have been processed. If they have not, control returns to block 15 to read in and process the next ΦA(I) element of the array in the third row 15 of the FIG. 1 data table. When all elements have been processed, control exits from the FIG. 2 data purification routine to data processing point 33 to proceed with the next (unrelated) task for the microprocessor.

If a data error has occurred ("YES" output of test 27 signalling that a data value ΦA(I) equaled the previous value), control passes to step 30 which replaces the assumed erroneous element ΦA(I−1)—(the value which should differ from ΦA(I) but did not) with the average of the two immediately contiguous elements, as by $$\Phi A(I-1) = (\Phi A(I) + \Phi A(I-2))/2. \qquad \text{Eq. 2.}$$

Accordingly, the data purification routine depicted in FIG. 2 and above-discussed replaces all error reading signifying ΦA(I)=1 values with an interpolated estimated value; and purges the data table row 14 ΦA(I) array of data of any contiguous equal values. The corrected set of ΦA(I) is shown in the third row 15 of the FIG. 1 data table. Thus, for example, the oscillation amplitude value during the cuff pressure step (time interval) "4" is corrected from the error-signalling +1 value to a peak amplitude 14, representing the average of measurements 4 and 25 at cuff pressures 187 Torr. and 153 Torr.during the immediately contiguous time intervals 3 and 5. Similarly, the first (pressure step 6) of two equal measured oscillation amplitude pulses of value 63 during periods 6 and 7, corresponding to occluding cuff pressures of 140 Torr. and 128 Torr., is corrected to a value of 44 representing the average of the contiguous measured amplitudes of 63 and 25 units.

The corrected array ΦA(I) as represented by the third row 15 in FIG. 1 thus comprises values from which each of the systolic, diastolic and mean arterial blood pressures may be determined either in accordance with the improved algorithms below discussed or employing the algorithms of the above referenced patents and patent applications. The data purification above discussed provides more accurate measurements than was heretofore the case; and also permits blood pressures to be determined more quickly, obviating the need for repeated deflation steps when unacceptable artifact or noise corrupted data is sensed.

Attention will now be shifted to the particular method pursuant to which the stored cuff pressure CP(I) and corrected blood pressure peak value ΦA(I) information in the first and third data rows of FIG. 1 is employed in accordance with other aspects of the present invention to measure a subject's systolic, diastolic and mean arterial blood pressures.

Figure 3:
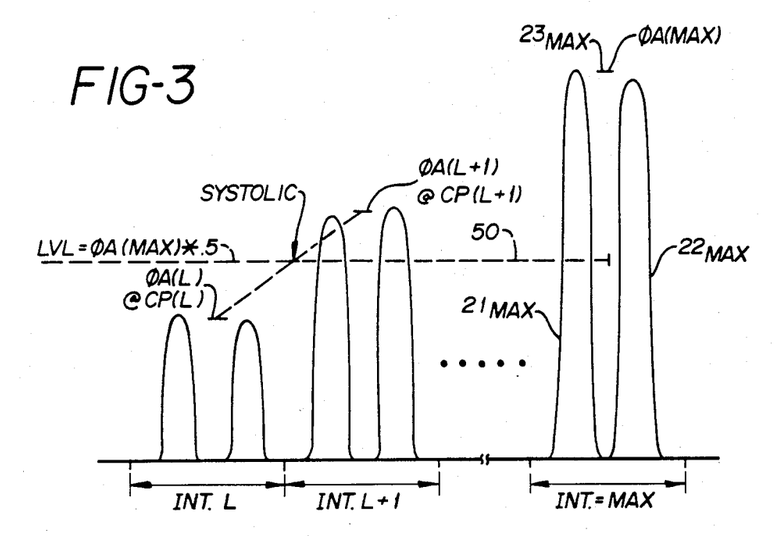
FIG. 3 depicts oscillation amplitude processing for a systolic blood pressure measurement in accordance with the present invention.
Figure 4:
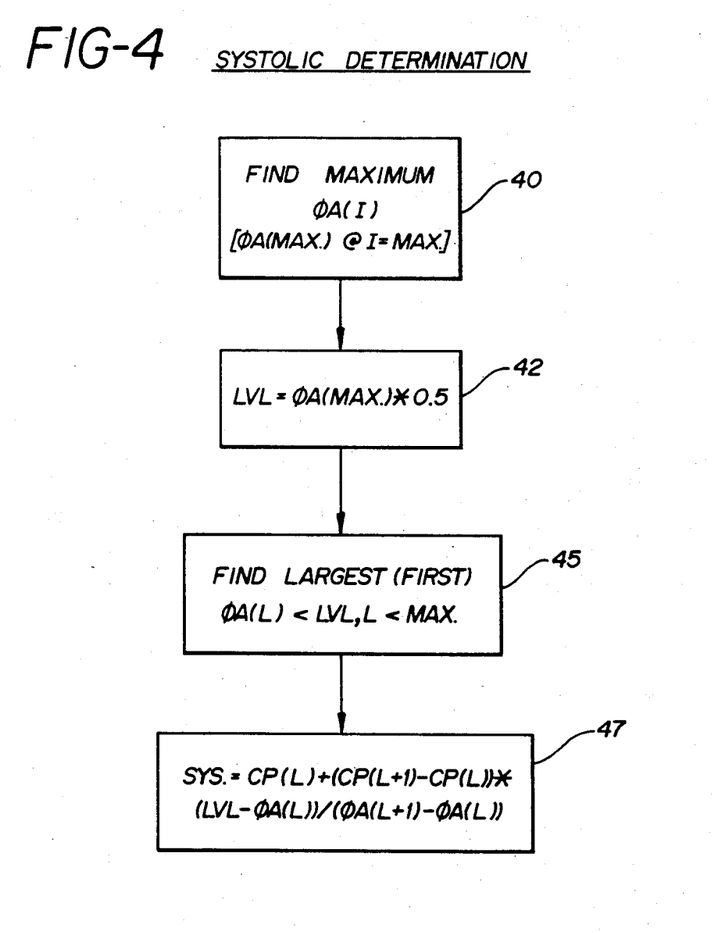
FIG. 4 is a program flow chart for the systolic blood pressure measurement typifield in FIG. 3.

Pulse complex wave form processing typifying systolic blood pressure determination is illustrated in FIG. 3, and a flow chart for the underlying data processing is set forth in FIG. 4. In overview, systolic pressure is determined by:

(a) Finding the amplitude (ΦA(MAX)) of the largest blood pressure oscillatory complex (which occurs at the time interval MAX):

(b) Finding an amplitude level (LVL) equal to a predetermined fraction of the peak value ΦA(MAX). We have found a value of 0.5 to be satisfactory for normal processing with something less (e.g., 0.45) for stat (rapid deflation and/or single pulse) operation:

(c) Examining the corrected oscillation amplitude (ΦA(I)) values (third row 15 in the FIG. 1 data table) starting at the MAX interval and proceeding toward the higher cuff pressure direction (i.e., to the left in FIGS. 1 and 3) to find the two contiguous oscillation amplitudes for which $$\Phi A(L) < \Phi A(MAX)^*0.5 < \Phi A(L+1); \qquad \text{Eq. 3.}$$

Figure 5:
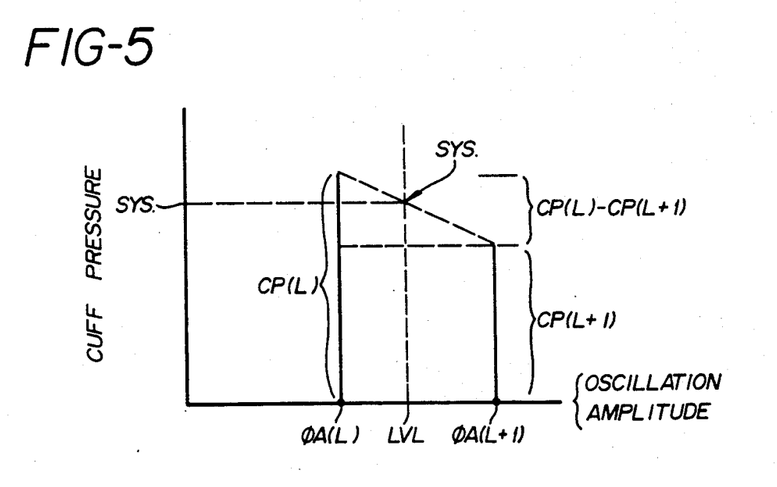
FIG. 5 illustrates blood pressure interpolation for the processing mode of FIGS. 3 and 4 (and by analogy for FIGS. 6-9 as well)

(d) Computing the interpolated cuff pressure (between CP(L) and CP(L+1)) assuming a linear variance in oscillation amplitude and cuff pressure between the intervals L and L+1. This per se well known linear trapezoidal interpolation is graphically depicted in FIG. 5. The interpolated cuff pressure directly corresponds to the subject's systolic blood pressure (SYS). Expanding upon the systolic pressure determining methodology set forth above, the cuff pressure interval I=MAX when the largest oscillation amplitude peak occurs is determined in any per se well known manner, (step 40 of the FIG. 4 flow chart corresponding to the interval MAX in FIG. 3).

Thus, for example, the following schematic BASIC sequence will suffice as illustrative to find the interval MAX:

| | |
|---|---|
| ΦAMAX=ΦA (1) | Eq. 4. |
| MAX=1 | Eq. 5. |
| FØR K=2 TØN | Eq. 6. |
| IF ΦA(K)<ΦAMAX GOTO 70 | Eq. 7. |
| ΦAMAX=ΦA(K) | Eq. 8. |
| MAX=K | Eq. 9. |
| 70 NEXT K | Eq. 10. |

In brief, Equations 4 and 5 make an initial assumption that the peak value occurred during the first interval and load a provisional peak value storing variable ΦAMAX with the value ΦA(1). For an assumed N-time interval measurement, the loop between Equations 6 and 10 sequentially examines every element of the ΦA(I) array from 2 to N, updating ΦAMAX only when the value ΦA(K)—(K being the loop index) exceeds the previously assumed ΦAMAX value. When the processing exits from the loop following instruction 70 in Equation 10 the variable MAX contains the value of I such that ΦA(MAX) is the largest value in the array.

The next following step 42 sets a variable LVL equal to the predetermined fraction of the peak amplitude ΦA(MAX) as by $$LVL = \Phi A(MAX)*0.5 \qquad \text{Eq. 11.}$$

The value LVL is shown by the dashed line 50 in FIG. 3.

The next following operation 45 finds the first time interval (L) preceding MAX for which the oscillation amplitude peak is less than LVL, i.e., less than one-half of the peak value ΦA(MAX), thereby finding the two contiguous values (L, L+1) having peak amplitudes which bound the value in LVL. Algorithms for conducting such a search are well known to those skilled in the art, e.g., $$\text{FOR } J = 1 \text{ TO MAX} \qquad \text{Eq. 12.}$$

$$\text{IF } (\Phi A(MAX-J)-LVL) < 0 \text{ GOTO } 140 \qquad \text{Eq. 13.}$$

$$\text{NEXT J} \qquad \text{Eq. 14.}$$

$$L = MAX - J \qquad \text{Eq. 15.}$$

Equations 12–15 simply comprise a DO or FOR-NEXT loop progressing from MAX−1 toward L=1, exiting when the first sub-LVL value is obtained. The appropriate interval identification (MAX−J) is stored in the variable location L.

Finally, the value of the systolic pressure is estimated by assuming a linear variation in cuff pressure between the values CP(L) and CP(L+1), and a linear variation between the corresponding oscillation amplitude ΦA(L) and ΦA(L+1). Thus, in accordance with the per se well known trapezoidal interpolation equation, the systolic pressure SYS may be determined (step 47 of FIG. 4) by $$SYS = CP(L) + \frac{(CP(L+1) - CP(L))*((LVL) - \phi A(L))}{\Phi A(L+1) - \Phi A(L)} \qquad \text{Eq. 16.}$$

To illustrate employing the data of FIG. 1, 50% of the peak amplitude (70) is 35, and thus the pulse complex measurements of time intervals 5 and 6 are selected for systolic pressure computation. The Eq. 16 software interpolation implementation yields:

$$SYS = 153 + ((140-153) \times (35-25)/(44-25)); \qquad \text{Eq. 17.}$$

$$= 146 \text{ Torr.} \qquad \text{Eq. 18.}$$

assuming three significant figures.

Figure 6:
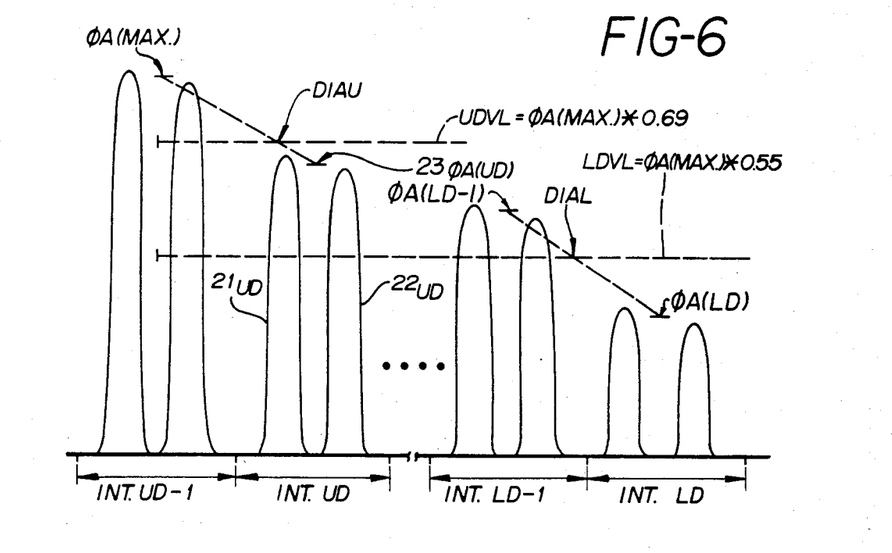
FIG. 6 depicts oscillatory complex measuring wave forms illustrating diastolic blood pressure determination in accordance with the present invention.
Figure 7:
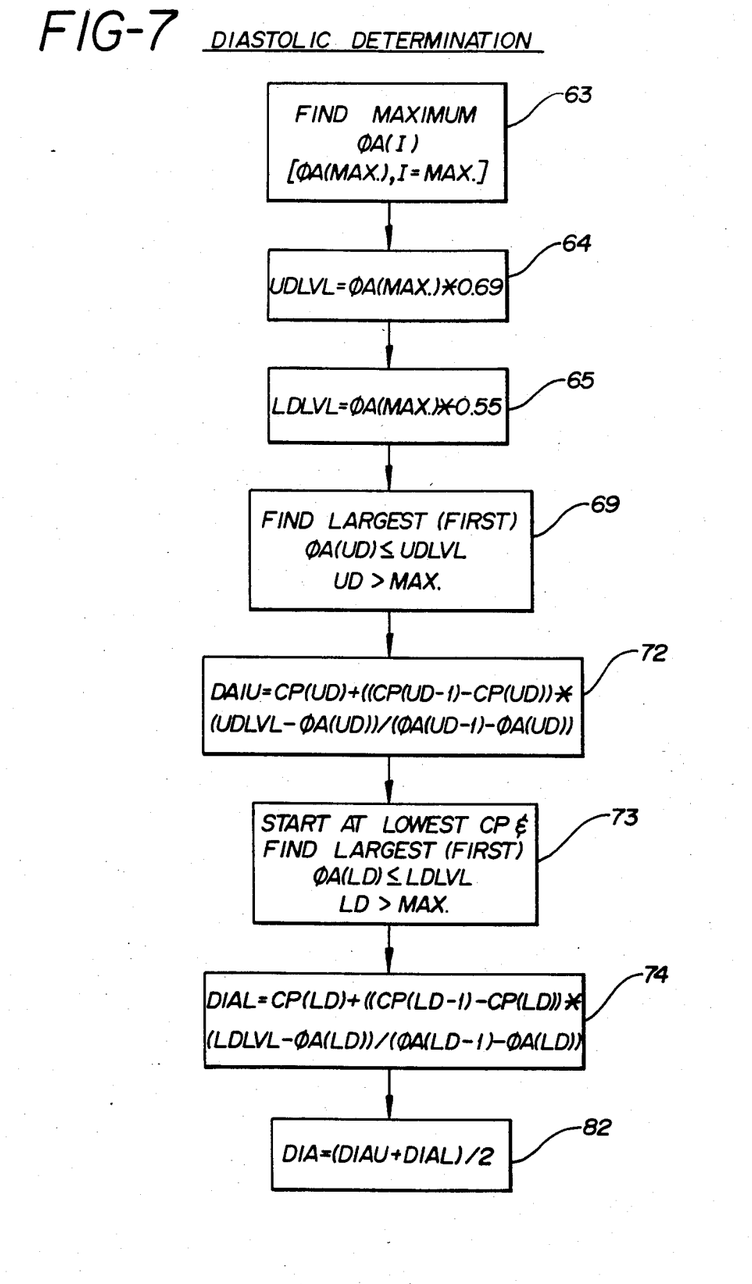
FIG. 7 is a program flow chart illustrating the diastolic blood pressure measurement typified by FIG. 6.

Pulse complex wave form processing characterizing diastolic blood pressure determination is illustrated in FIG. 6; and a flow chart for the underlying diastolic data processing algorithm is depicted in FIG. 7. In overview, diastolic pressure is determined by:

(a) the amplitude (ΦA(MAX)) of the complex (which occurs at the time interval MAX);

(b) Finding an amplitude level (UDLVL) equal to a first predetermined fraction of the peak value ΦA(MAX). We have found a value of 0.69 to be satisfactory for normal processing and 0.72 for rapid ("stat") processing;

(c) Examining the corrected oscillation amplitude (ΦA(I)) buffer 15 (FIG. 1) starting at the MAX interval and proceeding toward the lower cuff pressure direction (i.e., to the right in FIGS. 1 and 6) to find the two contiguous oscillation amplitudes for which $$\Phi A(UD) \leq \Phi A(MAX)*0.69 \leq \Phi A(UD-1); \qquad \text{Eq. 19.}$$

(d) Finding the interpolated cuff pressure (between CP(UD−1) and CP(UD)) assuming a linear variation in oscillation amplitude and cuff pressure between the intervals UD−1 and UD (processing variable DIAU in FIG. 7);

(e) Examining the stored ΦA(I) oscillation amplitude values at pressures starting at the lowest CP measured for a contiguous pair bounding the peak amplitude ΦA(MAX) multiplied by a second factor lower than the first factor (e.g., 0.55), i.e., where $$\Phi A(LD) \leq \Phi A(MAX)*0.55 \leq \Phi A(LD-1); \qquad \text{Eq. 20}$$

(f) Computing the interpolated cuff pressure between CP(LD) and CP(LD−1) corresponding to MAX times the 0.55 factor. This lower interpolated cuff pressure is associated with the variable designation DIAL; and (g) Determining the subject's diastolic pressure (DIA) as the average of the upper and lower interpolated values DIAU and DIAL, i.e., $$DIA = (DIAU + DIAL)/2. \qquad \text{Eq. 21.}$$

The above-described procedure is illustrated in the blood pressure complex depiction of FIG. 6 and the FIG. 7 flow chart. The peak ΦA(max) is first located as by the processing of Equations 4–10. The upper and lower peak amplitude fractions DIAU and DIAL are next determined (steps 64 and 65 of FIG. 7 corresponding to the labeled horizontal dash lines in FIG. 6). Step 69 then finds the first time interval (UD) following MAX at which the peak amplitude ΦA(UD) is lower than the value stored in DIAU (as by processing analogous to that of Equations 12 through 15 replacing "MAX−J" with "MAX+J"). Thereafter, step 72 performs the trapezoidal interpolation analogous to that of FIG. 5, determining the cuff pressure (DIAU) corresponding to the UDLVL complex amplitude value. It is observed that the time interval UD−1 coincides with the interval MAX when the peak complex value occurred since, for the data case illustrated, the first pulse complex following MAX less than 0.69×ΦA(MAX) occurred in the next time interval MAX+1.

The functional steps 73 and 74 of FIG. 7 perform in a manner directly analogous to operations 69 and 72. locating the cuff pressure DIAL by interpolation for the intervals when the peak complex amplitudes bound the LDLVL value equal ΦA(MAX) times 0.55. This latter search is conducted from ΦA(i) at the lowest CP, then working toward higher CP's. Finally, the subject's diastolic pressure (DIA) is computed as the average of the contents stored in DIAU and DIAL (step 82).

To illustrate with a numerical example, again employing the data portion of FIG. 1, $$DIAU = (83 + ((93-83) \times (48-40))/(40-53) = 77. \quad \text{Eq. 22.}$$

$$DIAL = 74 + (83-74) \times (38-33))/(33-40) = 67. \quad \text{Eq. 23.}$$

$$DIA = (71+67)/2 = 69. \quad \text{Eq. 24.}$$

Figure 8:
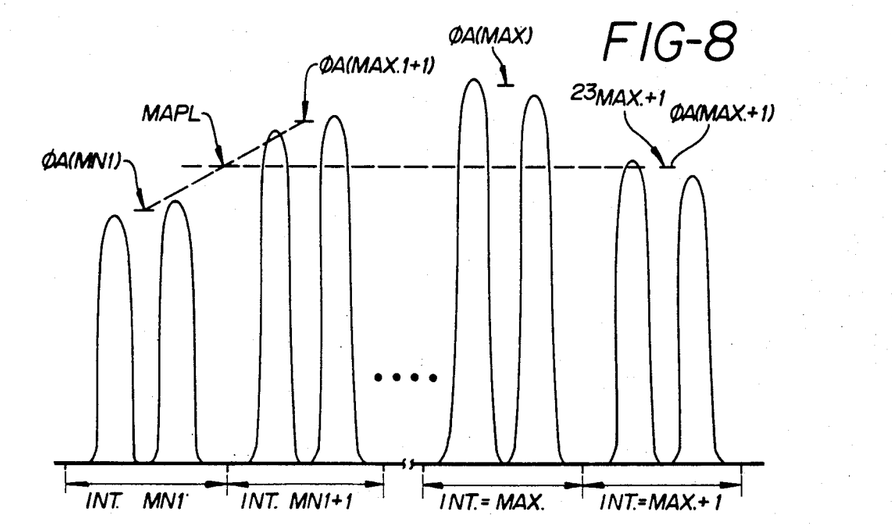
FIG. 8 is a timing diagram depicting oscillatory complex peak amplitude processing for mean arterial pressure measurements in accordance with the present invention.
Figure 9:
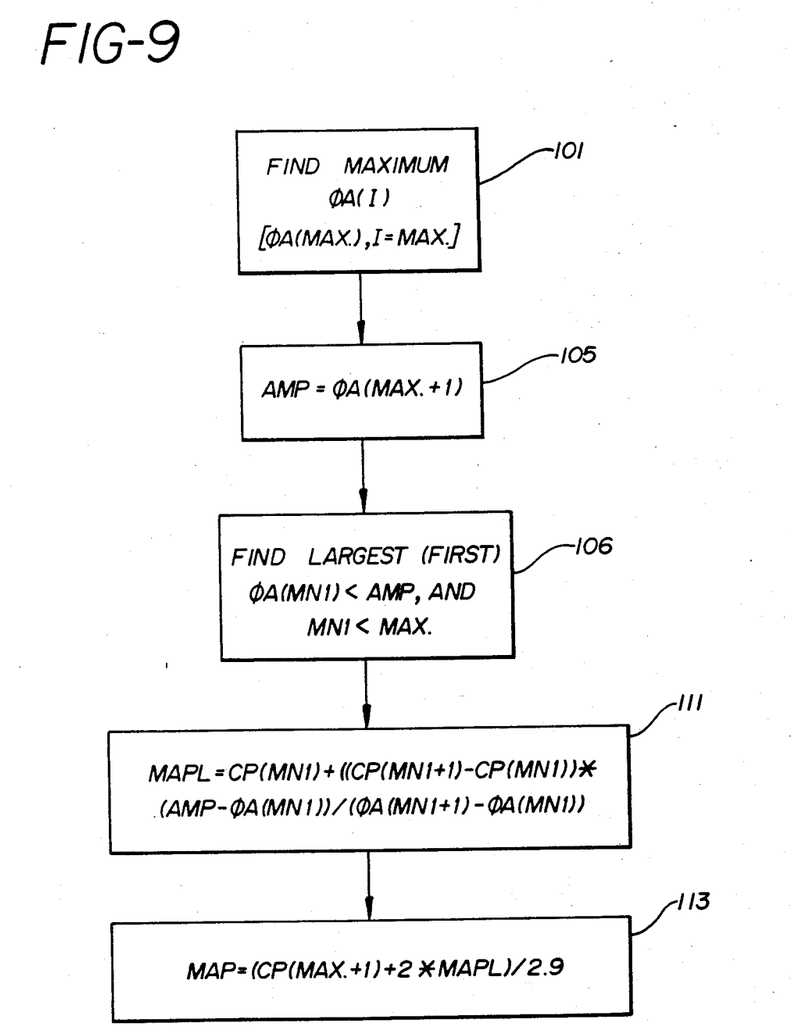
FIG. 9 is a program flow chart illustrating the mean arterial pressure determination typified by FIG. 8.

Finally, wave form processing illustrating mean arterial blood pressure measurement is shown in FIG. 8, and in flow chart form for the corresponding data processing in FIG. 9. In summary, means arterial pressure is determined by:

(a) Finding the amplitude ($\Phi A(MAX)$) of the largest complex (which occurs at the time interval MAX);

(b) Examining the cuff pressure values in the corrected register 15 (FIG. 1) for the interval MN1 yielding the first oscillation amplitude less than $\Phi A(MAX+1)$, i.e., the first cuff pressure to the left of the interval MAX which was less than the complex peak amplitude $\Phi A(MAX+1)$ occurring in the first interval following the time MAX. This satisfies the relationship $$\Phi A(MN1) \leq \Phi A(MAX+1) \leq \Phi A(MN1+1); \quad \text{Eq. 25.}$$

(c) An interpolation is then conducted between the intervals MN1 and MN1+1 for a cuff pressure MAPL corresponding to the oscillation amplitude value $\Phi A(MAX+1)$; and (d) Finally, the mean arterial pressure (MAP) is determined by a weighting of the cuff pressures CP(MAX+1) and MAPL, as by $$MAP = (CP(MAX+1) + (2*MAPL))/2.9 \quad \text{Eq. 26.}$$

The denominator (2.9 in Eq. 26) may be somewhat lower for operation in a "stat" mode, e.g., 2.85.

The above-discussed algorithm for determining mean arterial pressure is illustrated in FIGS. 8 and 9. Step 101 (FIG. 9) finds the peak interval MAX (for example, by execution comparable to Equations 4–10). A processing variable AMP is set equal to the peak value $\Phi A(MAX+1)$ of the complex following the interval MAX (step 105) and the interval MN1 is next determined (step 106) as the first occurring complex less than the value AMP (i.e., $\Phi A(MAX+1)$) to the left of time MAX in FIG. 8 (e.g., by processing comparable to Equations 12–15). An interpolation is then conducted to find the point MAPL (FIG. 8; step 111 in FIG. 9) and the final processing operation 113 finds the subject's mean arterial pressure by implementing Equation 26.

To again illustrate by numerical example from the FIG. 1 data $$MAPL = 140 + ((128-140) \times (62-44)/(63-44) = 129 \quad \text{Eq. 27.}$$

$$MAP = (140 + 2*129)/2.9 = 124 \quad \text{Eq. 28.}$$

The foregoing discussion has thus demonstrated that measured data may be enhanced by replacing data lost through measurement artifacts or the like or deviations from a proper data pattern by approximated values. Specific data processing algorithms were presented and discussed for the computation of a subject's measured systolic, diastolic and mean arterial blood pressures.

The above-described arrangements are merely illustrative of the principles of the present invention. Numerous modifications and adaptations thereof will be readily apparent to those skilled in the art without departing from the spirit and scope of the present invention. For example, the pressure measurement mode is described above as stepped deflation from an initial inflation above the subject's systolic pressure. The measurement of the instant invention can alternatively be performed by stepped inflation from an initial sub-diastolic cuff pressure; or via continuous vis-a-vis discrete cuff inflation or deflation.

What is claimed is:

1. In combination in digital processor controlled automated blood pressure measuring apparatus operative in conjunction with a stored program: (a) an inflatable cuff; (b) means for inflating and deflating said cuff; (c) pressure transducer means coupled to said cuff for signalling the pressure obtaining in said cuff; (d) means responsive to the pressure signalled by said transducer for generating a signal representing blood pressure complexes sensed by said cuff and said transducer coupled thereto; (e) complex peak storing means for storing values characterizing the peak amplitudes of said signals representing complexes at different cuff pressures; (f) cuff pressure storing means for storing the cuff pressures obtaining when said peak signals arose; and (g) diastolic pressure determining means, said diastolic pressure determining means comprising (i) means for locating the maximum peak amplitude stored in said cuff pressure complex peak storing means, (ii) computing means for computing two different levels each a different fraction of said maximum peak amplitude value, (iii) means for locating in said complex peak storing means two pair of entries each pair having one entry greater than and one entry less than a corresponding one of said two fractional values of said maximum peak amplitude, (iv) interpolation means operating upon said located peak pairs and upon the corresponding cuff pressures stored in said cuff pressure storing means for determining upper and lower intra-peak pressures, and (v) means responsive to said intra-peak pressures for determining diastolic pressure.

2. In combination in digital processor controlled automated blood pressure measuring apparatus operative in conjunction with a stored program; (a) an inflatable cuff; (b) means for inflating and deflating said cuff; (c) pressure transducer means coupled to said cuff for signalling the pressure obtaining in said cuff; (d) means responsive to the pressure signalled by said transducer for generating a signal representing blood pressure complexes sensed by said cuff and said transducer coupled thereto; (e) complex peak storing means for storing values characterizing the peak amplitudes of said signals representing complexes at different cuff pressures; (f) cuff pressure storing means for storing the cuff pressures obtaining when said pulse peak signals arose; (d) data purifying means operative upon values stored by said complex peak amplitude characterizing means pressure complex peak storing means for correcting data inaccuracies; and (h) diastolic pressure determining means, said diastolic pressure determining means comprising (i) means for locating the maximum peak amplitude stored in said complex peak storing means, (ii) computing means for computing two different levels during a given measurement cycle, each a different fraction of said peak amplitude value, (iii) means responsive to the values determined by said computing means for selecting from said complex peak storing means plural peak amplitudes generated at cuff pressures lower than that obtaining when said maximum cuff pressure pulse peak signal arose, and (iv) determining means for determining diastolic pressure from said selected plural amplitudes and the cuff pressures stored in said cuff pressure storing means corresponding to said selected plural signals.

3. A combination as in claim 2, wherein a preselected character is stored in said complex peak storing means to signal an unsuccessful cuff pressure flow peak measurement, and wherein said data correcting means comprises means for examining the contents of said complex peak storing means and responsive to detecting said preselected character for replacing said character with a measure of plural stored complex peak values at least one of which was obtained at a cuff pressure higher than that associated with the preselected character and at least one of which was obtained at a cuff pressure lower than that associated with the preselected character.

4. In combination in digital processor controlled automated blood pressure measuring apparatus operative in conjunction with a stored program; (a) an inflatable cuff; (b) means for inflating and deflating said cuff; (c) pressure transducer means coupled to said cuff for signalling the pressure obtaining in said cuff; (d) means responsive to the pressure signalled by said transducer for generating a signal representing blood pressure complexes sensed by said cuff and said transducer coupled thereto; (e) cuff pressure oscillation complex peak storing means for storing values characterizing the peak amplitudes of said signals representing complexes at different cuff pressures; (f) cuff pressure storing means for storing the cuff pressures; (g) second cuff pressure storing means for storing the cuff pressures obtaining when said peak amplitude signals arose; and (h) diastolic pressure determining means, said diastolic pressure determining means comprising (i) means for locating the maximum peak pulse amplitude stored in said cuff pressure oscillation complex peak storing means, (ii) computing means for computing two different levels each a different fraction of said maximum peak amplitude value, (iii) means responsive to the values determined by said computing means for selecting from said complex peak storing means plural peak amplitudes generated at cuff pressures lower than that obtaining when said maximum peak amplitude arose, wherein said plural signal selecting means comprises means for selecting four pulse peak signals stored in said cuff pressure storing means, two of said four values being larger than the two levels determined by said computing means and the other two of said four signals being smaller than the two levels selected by said computing means, and (iv) determining means for determining diastolic pressure from said selected plural peak amplitudes and the cuff pressures stored in said cuff pressures storing means corresponding to said selected plural signals.

5. A combination as in claim 4, wherein said determining means includes means for determining diastolic pressure operating upon said four complex peak amplitudes and upon the four cuff pressures stored in said cuff pressure storing means corresponding to said four stored complex peak values.

6. A combination as in claim 5, wherein a preselected character is stored in said complex peak storing means to signal an unsuccessful pulse flow peak measurement, and wherein said data correcting means comprises means for examining the contents of said complex peak storing means and responsive to detecting said preselected character for replacing said character with a measure of plural stored complex peak values at least one of which was obtained by the average of the cuff pressures next higher and next lower than that associated with the preselected character.

7. A combination as in claim 5, wherein said data purifying means includes means for searching said complex storing means for the occurrence of two equal peak amplitude values arising at successive cuff deflation pressures, and means responsive to said searching means for replacing one of the two stored equal values with a measure of the next higher of the next lower values stored in said complex peak storing means.

8. In combination in digital processor controlled automated blood pressure measuring apparatus operative in conjunction with a stored program; (a) an inflatable cuff; (b) means for inflating and deflating said cuff; (c) pressure transducer means coupled to said cuff for signalling the pressure obtaining in said cuff; (d) means responsive to the pressure signalled by said transducer for generating a signal representing blood pressure complexes sensed by said cuff and said transducer coupled thereto; (e) complex peak storing means for storing values characterizing the peak amplitudes of said signals representing complexes at different cuff pressures; (f) cuff pressure storing means for storing the cuff pressures obtaining when said peak signals arose; (g) data purifying means operative upon the complex peak amplitude characterizing values stored in said cuff pressure complex peak storing means for correcting data inaccuracies; and (h) diastolic pressure determining means, said diastolic pressure determining means comprising (i) means for locating the maximum peak pulse amplitude stored in said complex peak storing means, (ii) computing means for computing two different levels during a given measurement cycle, each a different fraction of said peak amplitude value, (iii) means responsive to the values determined by said computing means for selecting from said complex peak storing means plural peak amplitudes generated at cuff pressures lower than that obtaining when said maximum peak signal arose, and (iv) determining means for determining diastolic pressure from said selected plural signals and the cuff pressures stored in said cuff pressure storing means corresponding to said selected plural signals, (h) wherein said data purifying means includes (i) means for searching said complex storing means for the occurrence of two equal peak amplitude values arising at successive cuff deflation pressures, and (ii) means responsive to said searching means for replacing one of the two stored equal values with a measure of two other values stored in said complex peak storing means.

9. In an automated oscillometric blood pressure unit employing an arterial occluding cuff and means for controllably inflating said cuff at least to mean arterial pressure, a method for measuring diastolic pressure comprising the steps of:
 (a) measuring cuff pressure oscillation peak amplitudes, and each respectively associated cuff pressure level at predetermined increments between cuff deflation pressure and mean arterial pressure;
 (b) commencing with a specified maximum amplitude near mean arterial pressure, and proceeding toward cuff deflation pressure, identifying a first pair of contiguous ones of said amplitudes having a predetermined first fractional relationship to said specified maximum amplitude near mean arterial pressure;

(c) interpolating said first pair of contiguous amplitudes;

(d) commencing with a specified minimum amplitude, and proceeding toward maximum cuff pressure, identifying a second pair of contiguous ones of said amplitudes having a second predetermined fractional relaionship to said specified maximum amplitude;

(e) interpolating said second pair of contiguous amplitudes; and (f) identifying diastolic pressure as the pressure corresponding to a predetermined weighted average of said respective interpolated values.

* * * * *

UNITED STATES PATENT AND TRADEMARK OFFICE
CERTIFICATE OF CORRECTION

PATENT NO. : 4,638,810

DATED : January 27, 1987

INVENTOR(S) : Maynard Ramsey III et al.

It is certified that error appears in the above-identified patent and that said Letters Patent is hereby corrected as shown below:

Claim 2, column 12, line 59, "(d)" should be --(g)--.

Claim 6, column 14, line 1, "tosignal" should be --to signal--.

Signed and Sealed this

Twenty-fifth Day of July, 1989

Attest:

Attesting Officer

DONALD J. QUIGG

Commissioner of Patents and Trademarks